US009234860B2

(12) United States Patent
Pfauch et al.

(10) Patent No.: US 9,234,860 B2
(45) Date of Patent: Jan. 12, 2016

(54) PROBE SYSTEM FOR MEASURING A MEASURED VARIABLE OF A PROCESS MEDIUM CONTAINED IN A PROCESS CONTAINER

(75) Inventors: Thomas Pfauch, Leipzig (DE); Ingrid Wunderlich, Radebeul (DE); René Kundscher, Radeburg (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 786 days.

(21) Appl. No.: 13/454,144

(22) Filed: Apr. 24, 2012

(65) Prior Publication Data

US 2012/0272756 A1 Nov. 1, 2012

(30) Foreign Application Priority Data

Apr. 26, 2011 (DE) .......................... 10 2011 017 535

(51) Int. Cl.
    *G01D 11/24* (2006.01)
    *G01N 27/28* (2006.01)

(52) U.S. Cl.
    CPC .................................... *G01N 27/283* (2013.01)

(58) Field of Classification Search
None
See application file for complete search history.

(56) References Cited

U.S. PATENT DOCUMENTS

| 4,438,399 A | 3/1984 | Schnabl |
| 5,011,587 A * | 4/1991 | Schmidt .................... 204/401 |
| 2007/0034028 A1* | 2/2007 | Tottewitz et al. ............ 73/866.5 |
| 2009/0214387 A1 | 8/2009 | Straub |
| 2010/0117439 A1 | 5/2010 | Klabisch |
| 2011/0189050 A1 | 8/2011 | Schlereth |
| 2011/0290045 A1 | 12/2011 | Hanko |

FOREIGN PATENT DOCUMENTS

| DE | 2837486 | | 3/1980 |
| DE | 3635150 | A1 | 5/1987 |
| DE | 102005048332 | A1 | 4/2006 |
| DE | 102005036865 | A1 | 2/2007 |
| DE | 102005051279 | A1 | 5/2007 |
| DE | 102006011904 | A1 | 9/2007 |
| DE | 202007006784 | U1 | 10/2007 |
| DE | 102006022983 | A1 | 11/2007 |
| DE | 102006048898 | A1 | 4/2008 |
| DE | 202008003764 | U1 | 6/2008 |

(Continued)

*Primary Examiner* — Robert R Raevis

(74) *Attorney, Agent, or Firm* — Bacon & Thomas, PLLC

(57) ABSTRACT

A probe system, including: a connector apparatus; a treatment chamber part having at least one treatment medium supply line communicating with the treatment chamber; a measuring head seated so as to be axially shiftable, and a treatment position, wherein the immersion tube, on its connector apparatus-side front end, has a front-end closed, protective cylinder, and is arranged in a section of the immersion tube, so that, in the measuring position of the immersion tube, the measuring head is contactable via perforations with the process medium, and in the treatment position of the immersion tube, is contactable with the treatment medium; and a drive system for axial shifting of the immersion tube, arranged on the end region of the probe system facing away from the connector apparatus. The treatment chamber part is surrounded by a support structure connected with the connector apparatus and with the drive system.

20 Claims, 5 Drawing Sheets

(56) References Cited

FOREIGN PATENT DOCUMENTS

| | | |
|---|---|---|
| DE | 20007006122 U1 | 7/2008 |
| DE | 102007034268 B3 | 10/2008 |
| DE | 102007030584 A1 | 1/2009 |
| DE | 102009020440 A1 | 12/2010 |
| DE | 102009033558 A1 | 1/2011 |
| DE | 102009045472 A1 | 4/2011 |
| DE | 102009045579 A1 | 4/2011 |
| DE | 102010001391 A1 | 8/2011 |
| DE | 102010001779 A1 | 8/2011 |
| DE | 102010001876 A1 | 8/2011 |
| DE | 102010028572 A1 | 11/2011 |
| DE | 102010029029 A1 | 11/2011 |
| EP | 1156323 A1 | 11/2001 |
| EP | 2278312 A1 | 1/2011 |
| WO | 2004023127 A1 | 3/2004 |
| WO | WO2009/115282 A1 | 9/2009 |
| WO | WO2011042241 A1 | 4/2011 |
| WO | WO2011138158 A1 | 11/2011 |

* cited by examiner

PROBE SYSTEM FOR MEASURING A MEASURED VARIABLE OF A PROCESS MEDIUM CONTAINED IN A PROCESS CONTAINER

TECHNICAL FIELD

The invention relates to a probe system for measuring a measured variable of a process medium contained in a process container, especially for application in chemical, foods, biotechnological or pharmaceutical processes.

BACKGROUND DISCUSSION

The field of use of probe systems for measuring physical or chemical measured variables of a medium in process measurements technology is manifold. For example, chemical, foods, biotech or pharmaceutical processes require the use of measuring probes for monitoring the process or a product manufactured in the process. The measuring probes can, for example, be pH-measuring probes, ion-selective electrodes, conductivity probes, turbidity probes, or optical or electrochemical measuring probes for determining a concentration of a substance contained in the process medium to be monitored, such as $O_2$, $CO_2$, certain ion types or organic compounds.

From the state of the art, it is known to perform on process media inline measurements, in the case of which probe systems with an axially movable immersion tube holding a measuring probe come into use. Such probe systems are also referred to as retractable assemblies. These retractable assemblies are secured on a process container, for example, or a pipe conveying the process medium. They have a treatment chamber, into which the measuring probe can be moved temporarily during operation by means of the immersion tube. Into the treatment chamber, different treatment media can be introduced. For example, a rinsing liquid for cleaning the measuring probe can be conveyed through the treatment chamber. Also a supplying of the measuring probe with a sterilization medium, e.g. superheated steam, is possible in the treatment chamber, Finally, also a calibration liquid can be conveyed into the treatment chamber, in order to conduct a calibration of the measuring probe. After termination of the treatment, the measuring probe is moved back into the process container or into the process medium, in order to continue with the inline measurement. In such case, a contamination of the process medium to be monitored, or, conversely, a contamination of the calibration liquid with process medium, is counteracted with the assistance of seals, which seal off the treatment chamber and the process container from one another.

For many processes, especially in foods technology, pharmacy and biotechnology, even slight contaminations from the dissolving out of substances from the process container or medium-contacting parts of the probe system are not tolerable. Other processes, especially also for cleaning the process container, use aggressive media, which can attack the medium-contacting parts of the probe system and lead to undesired corrosion. Chemically resistant materials, with which these problems can be prevented, are, for example, titanium or highly corrosion-resistant nickel-chromium-molybdenum-tungsten alloys. These materials are, however, very expensive. Largely chemically inert synthetic materials, or plastics, such as e.g. PTFE, PFA or PVDF, frequently have a significantly smaller mechanical strength in comparison to metals and metal alloys.

In DE 10 2009 033 558 A1, a probe system of the previously named type is described, which is designed for connection to an Ingold nozzle of a process container. The probe system includes a plug part inserted in the connected state into the Ingold nozzle, which is composed of an outer holding ring, made of metal and securable with a coupling nut on the Ingold nozzle, and, anchored in the holding ring, a plug made of synthetic material and insertable in the Ingold nozzle. The synthetic material of the plug should be suitable for application in aggressive process media, while the metal holding ring should assure a sufficient strength for a robust and stable holding of the retractable assembly by means of the coupling nut.

For cleaning and/or calibrating the measuring probe, the probe system includes a rinsing/washing chamber part, in which a rinsing chamber is placed, which is sealed by seals on the process side against the process medium. In the case of retracting the immersion tube with the measuring probe into the rinsing chamber, it is unavoidable that process medium also gets displaced into the rinsing chamber. Thus, also the rinsing chamber is to be taken into consideration as a medium-contacting end component of the probe system. DE 10 2009 033 558 A1 does not, however, also provide that the rinsing chamber is manufactured from an inert material. In the probe system described there, the rinsing chamber is formed in a sleeve part of the probe assembly, which is secured by means of an additional coupling nut on a pneumatic drive of the immersion tube. For this reason, the sleeve part must be embodied in a relatively solid and mechanically stable form. An embodiment of the sleeve part made of titanium or highly corrosion-resistant materials would, for reasons of cost, be disadvantageous. An embodiment using synthetic material would not assure the required mechanical stability.

SUMMARY OF THE INVENTION

It is, consequently, an object of the invention to provide a probe system, which overcomes the disadvantages of the state of the art. The probe system should especially permit, in the case of simple construction, an embodiment of the components coming in contact with the process medium during operation made from a material with sufficient chemical durability, while assuring the robustness and mechanical stability required for use in process measurements technology.

This object is achieved by a probe system as claimed in claim 1.

Such a probe system for measuring a measured variable of a process medium contained in a process container includes:
- a connector apparatus connectable with a complementary connecting means of the process container,
- a treatment chamber part forming a treatment chamber and having at least one treatment medium supply line communicating with the treatment chamber,
- a measuring probe with a measuring head embodied for registering measured values, wherein the measuring probe is accommodated in an immersion tube, which is seated so as to be axially shiftable between a measuring position, in which the measuring head is outside of the treatment chamber, and a treatment position, in which the measuring head is retracted into the treatment chamber, wherein the immersion tube, on its connector apparatus-side front end, has a front-end closed, protective cylinder, and wherein the measuring head is arranged in a perforated section of the immersion tube behind the protective cylinder, so that, in the measuring position of the immersion tube, the measuring head is contactable via perforations with the process medium, and in the treatment position of the immersion tube, is contactable with the treatment medium, and a drive system for axial shifting of the immersion tube, arranged on the end region of the probe system facing away from the connector apparatus, wherein the treatment chamber part is surrounded by a support structure connected with the connector apparatus and with the drive system.

Since the treatment chamber part is surrounded by a support structure connected with the connector apparatus and the drive system, the support structure performs a stabilizing function for the treatment chamber part arranged between the connector apparatus and the drive system. The treatment chamber part alone thus need not bear the weight of the drive system, and can, consequently, be made of a softer material or be embodied in a more thin-walled manner, than would be the case without the additional support structure. Thus, the treatment chamber part itself can be formed of a largely chemically inert synthetic material, or alternatively from one of the higher priced, highly corrosion-resistant metal materials, especially a highly corrosion-resistant alloy, such as Hastelloy, wherein the wall of the treatment chamber part can, in the latter case, be embodied in a very thin manner, in order to save material, and therewith costs.

As a chemically inert material, PVDF (polyvinylidene fluoride), PEEK (polyetheretherketone), PFA (perfluoroalkoxy alkane) or PTFE (polytetrafluoroethylene), for example, come into question. As metal corrosion-resistant materials, highly corrosion-resistant nickel-chromium-molybdenum-tungsten alloys, such as 2.4602 or Hastelloy or titanium come into question.

By "a chemically inert material" is especially meant here a material, which is chemically resistant against the process medium contained in the process container and/or against the treatment media supplied to the treatment chamber during operation of the probe system. The chemically inert material should especially be formed in such a manner that it neither enters into chemical reactions with these media, nor that substances dissolve from the material into the media. Furthermore, the absorbing of process medium or washing/rinsing medium or its components by the material should be prevented, i.e. the material must not be porous nor form pores in the course of time due to corrosion.

All medium-contacting components of the probe system, i.e. all components, which, in a position of the immersion tube, especially in the measuring position, the treatment position, or, in the case of shifting of the immersion tube between the measuring position and the treatment position, come in contact with the process medium, can, in an advantageous embodiment, be formed from such chemically inert material. In such case, the different medium-contacting components can be formed from different inert materials, e.g. depending on the specific mechanical requirements, which are to be placed on the individual components. it is, however, also possible that all medium-contacting components of the probe system are formed from the same material as the treatment chamber part.

The drive system is preferably embodied as a linear drive and includes a movable part, which, for example, can comprise a push rod, and an immovable part, in which a bearing for the movable part is formed. The support structure is in this embodiment firmly and/or releasably connected with the immovable part.

The immersion tube, as a likewise medium-contacting end component can, in its entirety, be formed from a chemically inert material. Advantageously, the immersion tube can be composed of a plurality of components made of different materials. For example, the medium-contacting, connector apparatus-end front end, which includes the protective cylinder and the section of the immersion tube having perforations and arranged behind the protective cylinder, can be formed as a first component made of a chemically inert material, and connected with a second, drive side component made of a mechanically stable, and not necessarily chemically inert material. On the one hand, this embodiment permits a mechanically stable and robust connection of the immersion tube with the drive system, and, on the other hand, a sufficient chemical stability of the medium-contacting front end against the process medium or the treatment medium is assured.

The support structure can be embodied as a sleeve at least sectionally having a tubular wall and accommodating the treatment chamber part, and having at least one passageway extending through the wall, wherein the treatment chamber part and the support structure are arranged, secured against twisting, in an orientation to one another, in which the passageway aligns with the treatment medium supply line communicating with the treatment chamber. The passageway extends preferably in a radial direction, so that the treatment medium can be brought via a supply line connection arranged laterally on the support structure into the treatment chamber. As a twist-preventer between the support structure and the treatment chamber part can serve, for example, at least one radially movable blocking member arranged in the support structure, especially a pin connection—for example, by means of a set pin—which engages into a cavity of the treatment chamber part.

The support structure can have an annular area, which is formed by an annular step in its inner wall, which faces toward the connector apparatus, and which abuts on an apparatus annular shoulder in an end region of the treatment chamber part facing away from the connector apparatus and formed by a lessening of the outer diameter of the treatment chamber part. In this way, by means of the support structure, the treatment chamber part is secured in a shape-interlocking manner on the connector apparatus of the probe system.

In an embodiment, the connector apparatus can comprise a flange connected with the support structure, which is connectable, with interpositioning of an annular gasket, to a flange of the process container complementary thereto.

The connector apparatus-end of the treatment chamber part can have an annular shoulder, which sits in a seat formed by a nozzle of the gasket extending in an axial direction, wherein the gap formed between the seat and the treatment chamber part is sealed from the process container by means of at least one ring seal.

The treatment chamber part can have in the end region of its connector apparatus end at least one internally lying seal bearing against the immersion tube, which, both in the measuring position, as well as also in the treatment position, of the immersion tube, seals off the treatment chamber from the process container.

The seat formed in the nozzle of the gasket extending in an axial direction or the connector apparatus-end of the treatment chamber part can have a cavity, for example, an annular shoulder or an annular groove, in which a wiping ring bearing against the immersion tube is accommodated. The wiping ring can also be held between an end face of the treatment chamber part facing the process container and an area of an annular step formed in the inner wall of the axial nozzle of the gasket and lying opposite this end face.

The gasket can be formed as a media-contacting component made of a chemically inert material. It can especially be composed of the same material as the treatment chamber part.

In an embodiment adapted for connection of the probe system to a complementary nozzle of a process container, the treatment chamber part includes on its connector apparatus-end a plug-like projection, which is embodied so as to enter into the nozzle of the process container, wherein the connector apparatus includes a holding ring, which is securable by means of a coupling nut on the complementary nozzle, and which has an annular area facing away from the process container, on which an annular step formed in the outer wall of the treatment chamber part adjoins.

In this embodiment, the support structure is connected with the side of the holding ring facing the drive system, wherein the support structure has a ledge surface facing the connector apparatus. The ledge surface bears against an annular shoulder of the treatment chamber facing away from the connector apparatus, in order further to stabilize the treatment chamber part.

BRIEF DESCRIPTION OF THE DRAWINGS

Other features, details and advantages of the invention will now be explained in greater detail on the basis of the appended drawing, the figures of which show as follows.

DETAILED DISCUSSION IN CONJUCNTION WITH THE DRAWINGS

Figure 1:
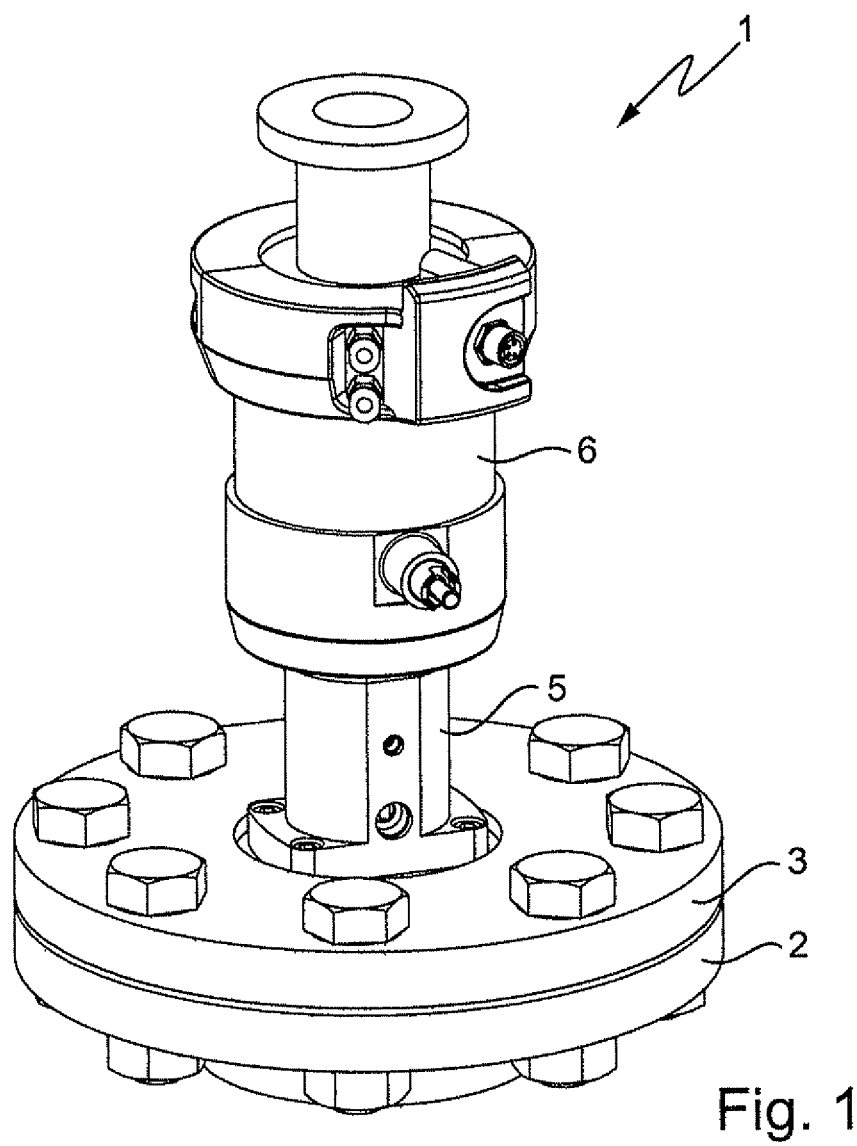
FIG. 1 a probe system according to a first embodiment for connection to a flange of a process container.

FIG. 1 shows a probe system 1 connected to a flange 2 of a process container (not illustrated in greater detail). For connection to the flange 2 of the process container, the probe system 1 includes a connector apparatus with a complementary flange 3. Connected with the flange 3 is a support structure 5, which surrounds and stabilizes a treatment chamber part 4 (not visible in FIG. 1) arranged therein. On its end facing away from the connector apparatus, the support structure 5 is connected with a drive system of the probe system 1. In the example shown here, the drive system includes a pneumatic drive with a cylinder 6, in which a piston (not shown) is seated in an axially movable manner, which divides the cylinder 6 into two pressure chambers. Via pressure loading of one the two respective pressure chambers, the piston can be moved axially within the cylinder in the direction of the other respective pressure chamber. The piston is connected with an immersion tube 7, so that the immersion tube, by means of the axial piston movement, likewise can be moved in an axial direction and can be retracted into or extended out from the treatment chamber part 4. A detailed description of such a pneumatic drive for a probe system of the previously named type can be found, for example, DE 20 2007 017 297 U1. The drive system can alternatively also be embodied for manual actuation, or in some other manner. In this case, the support structure can be connected with a locationally fixed component of the drive system directly, or via a number of intermediate pieces.

Figure 2:
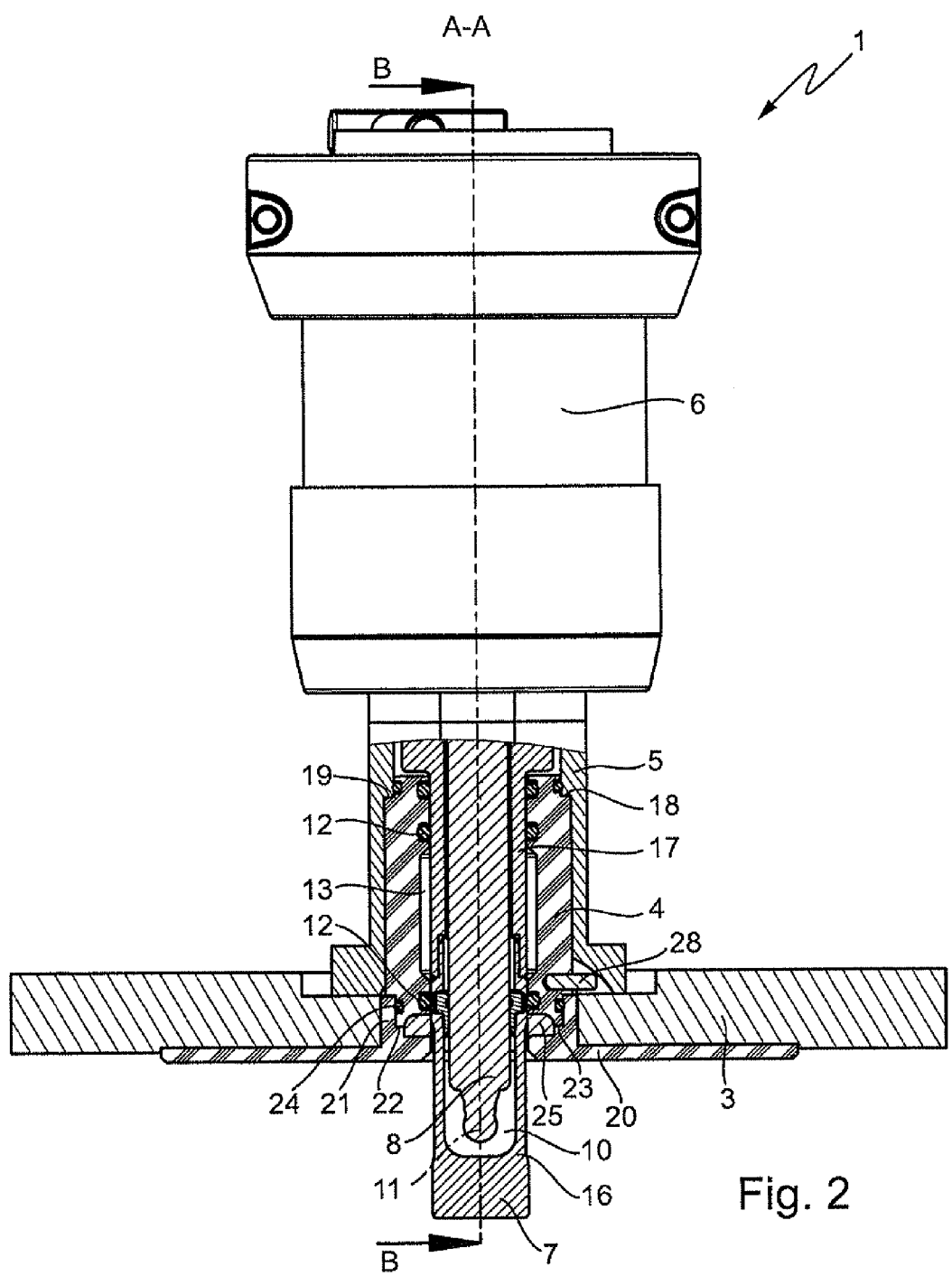
FIG. 2 the probe system shown in FIG. 1, in a longitudinal section.
Figure 3:
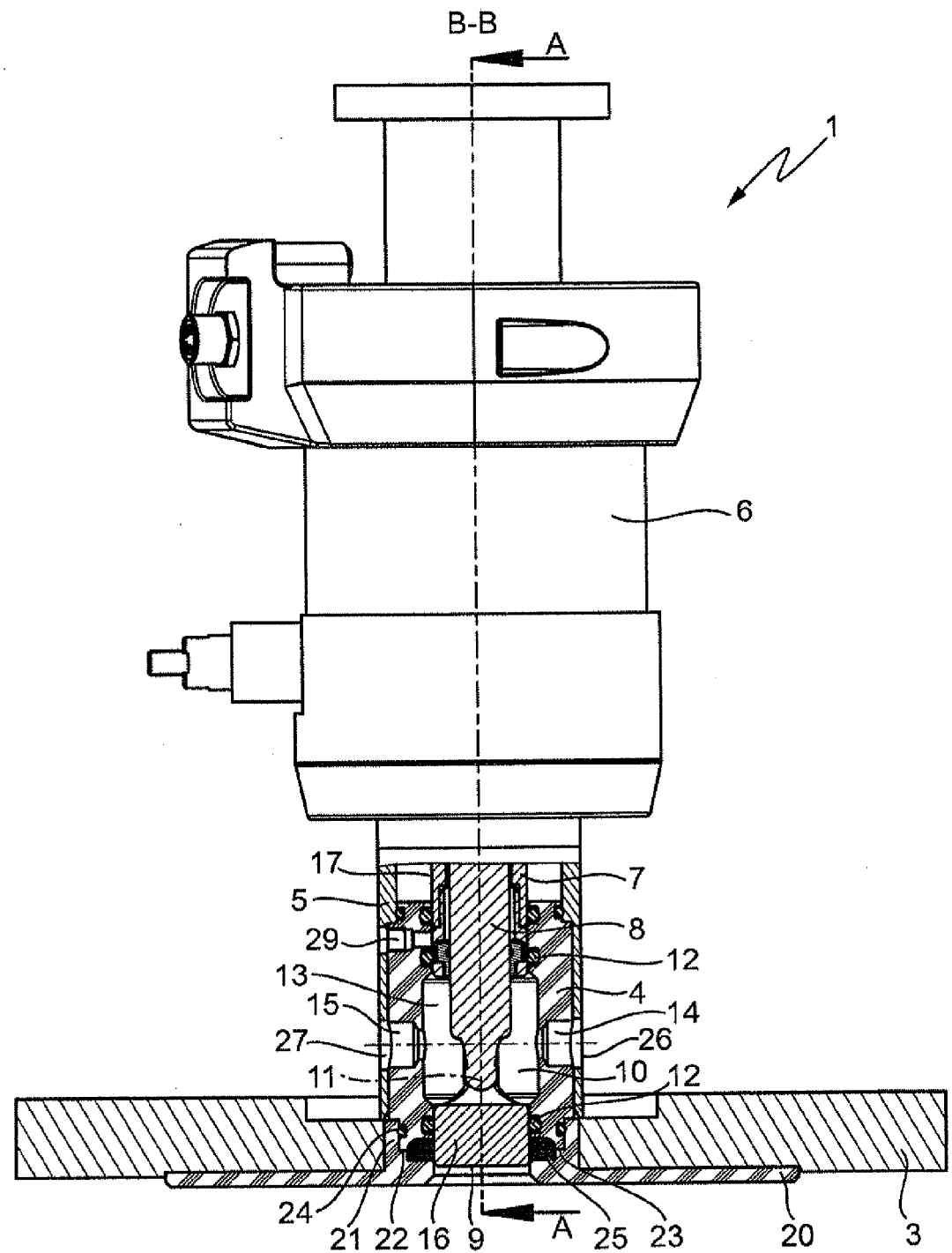
FIG. 3 the probe system shown in FIG. 1, in a longitudinal section taken in a cutting plane perpendicular to the longitudinal section of FIG. 2.

FIGS. 2 and 3 show longitudinal sections through the probe system 1 of FIG. 1, taken along two cutting planes A-A and B-B extending perpendicular to one another.

The probe system 1 includes an immersion tube 7 movable in an axial direction. Arranged in the immersion tube 7 is a measuring probe 8, for example, a pH-measuring, glass electrode. Immersion tube 7 is guided in an axially displaceable manner in the treatment chamber part 4, which is embodied as an essentially tubular sleeve. On two end sections of the treatment chamber part 4 lying opposite one another, the annular gap formed between the treatment chamber part 4 and the immersion tube 7 is, in the measuring position and in the treatment position, sealed in a liquid-tight manner from the process container and, respectively, from the drive system by sealing rings 12 in each case accommodated in an annular groove in the inner lateral surface of the treatment chamber part, adjoining the immersion tube 7. In a section of the treatment chamber part 4 arranged between the sealing rings 12, the inner diameter of the treatment chamber part 4 widens, so that in this section between the immersion tube 7 and the treatment chamber part 4, an annular chamber is formed, which is sealed off from the process container by the process-side sealing ring 12, this annular chamber serving as a treatment chamber 13.

The immersion tube 7 is, in the present example, constructed of a plurality of parts. The front end of the immersion tube 7 coming in contact with the process medium in the measuring position is formed of a first immersion tube part 16 made of a chemically inert material, for example, a synthetic material such as PFA, PTFE or PEEK, or a metal such as titanium, or a highly corrosion-resistant alloy such as Hastelloy. It can be connected with an additional, rear-side immersion tube part 17 not coming in contact with the process medium or treatment medium, for example, via a screw thread connection or a bayonet connection. The additional immersion tube part 17 need not be composed of an especially inert material. It can, for example, be formed of a high quality alloy steel, even stainless steel. This additional immersion tube part 17 is connected with the drive system 6 directly, or via additional intermediate pieces. If the drive system comprises, for example, a pneumatic drive as described above, the additional immersion tube part 17 is connected with the piston, which, in turn, is movable within the pneumatic cylinder. In this way, it is, on the one hand, assured that the medium-contacting part of the immersion tube does not in interact in an undesired manner with the process medium and/or treatment medium, and, on the other hand, a mechanically sufficiently robust and stable connection of the immersion tube with the drive is assured. At the same time, also the amount of the cost-intensive, highly corrosion-resistant material used in certain circumstances for the medium-contacting region of the immersion tube is minimized.

FIG. 2 shows the immersion tube 7 in a measuring position, extended out from the treatment chamber part 4; FIG. 3 shows the same in a treatment position, retracted into the treatment chamber part. On its connector apparatus-side front end, the immersion tube 7 includes a front-side, closed protective cylinder 9. The measuring head 11 of the measuring probe 8 is arranged in a section of the immersion tube following behind the protective cylinder 9, this section of the immersion tube having perforations 10, via which the measuring head 11 is contactable with a liquid or gaseous medium. In the measuring position (FIG. 2), the section of the immersion tube 7 having the perforations 10 is located within the process container, so that the measuring head 11 can be supplied with the process medium contained in the process container. In the treatment position (FIG. 3), the measuring head is located within the treatment chamber 13, which, also in this position of the immersion tube 7, is sealed from the process container by the process-side sealing ring 12 abutting against the protective cylinder 9 of the immersion tube 7.

For supplying a treatment medium, for example, a cleaning or calibration liquid or a sterilization medium, into the treatment chamber 13, the treatment chamber part 4 includes a passageway 14 extending in a radial direction (FIG. 3), which opens into the treatment chamber 13. Via the perforations 10, the measuring head 11 can be supplied in the treatment position with the treatment medium. For removing the treatment medium, the treatment chamber part 4 includes an additional passageway 15 likewise extending in a radial direction into the treatment chamber 13. Preferably, passageway 15 lies opposite the first passageway 14. The passageways 14 and 15 can, in other embodiments, also be inclined at an angle relative to the radial direction. For cleaning the seals 12 or a section of the immersion tube 7 arranged behind the non-process-side seal 12, one or more further supply lines 29 can be provided in an end region of the treatment chamber part 4 away from the connector apparatus.

In the case of retraction of the front end of the immersion tube 7 with the measuring head 11 into the treatment chamber 5, process medium can escape from the process container into the treatment chamber 13. The treatment chamber part 4 is, for purposes of protection against an attack of aggressive process media, consequently formed of a chemically inert material, especially a synthetic material, such as PFA, PVDF, PTFE or PEEK. Alternatively, it can also be formed of a highly corrosion-resistant metal such as titanium, or a highly corrosion-resistant alloy, e.g. Hastelloy, wherein a minimizing of the expensive metal material is attainable by using as low a wall thickness as possible. For assuring a sufficient stability of the probe system 1 in spite of lesser mechanical stability of the synthetic materials or due to a small wall thickness of the treatment chamber part 4, the treatment chamber part 4 is surrounded by the support structure 5. The support structure 5 is connected on the connector apparatus-side with the flange 3 provided for connection to the process container, and is embodied so as to hold the treatment chamber part 4 in a shape-interlocking manner on its end away from the connector apparatus, and thus to affix it. On its end facing away from the process container, the support structure 4 is connected with the cylinder 6 of the drive system. In the present example, the support structure 5 is embodied as a one-piece, tubular sleeve surrounding the treatment chamber part 4. It can, for example, be composed of stainless steel. On its connector apparatus-end, the support structure 5 is connected with the flange 3 in a releasable but stable manner via a screwed connection. On its opposite-lying side facing away from the connector apparatus end, by means of one or more screws or by means of a coupling nut, the support structure 5 can likewise be secured to the drive system; in the present case, to the pneumatic cylinder. In the end region of the treatment chamber part 4 facing away from the connector apparatus, the outer diameter of the treatment chamber part 4 tapers abruptly, so that an annular shoulder 18 is formed, on which an abutment surface 19 facing the process connection and formed in the inner wall of the support structure 5 abuts. On its end facing the process connection, the treatment chamber part 4 is supported by a gasket 20 affixed between the flange 3 of the connector apparatus of the probe system 1 and the flange 2 of the process container.

The gasket 20 is, in the example shown here, composed of the same material as the treatment chamber part 4, especially of a synthetic material such as PFA, PTFE, PVDF or PEEK. It includes an annular, washer-shaped region, this region extending between the flange 2 of the process container and the flange 3 the probe system 1, and serving as a sealing element for the flange connection with the process container. Furthermore, the gasket 20 includes a nozzle 21 extending in an axial direction, which protrudes inwardly into the central opening of the flange 3. The nozzle 21 forms an annular seat 22, in which sits an annular shoulder 23 formed in the connector apparatus-end region of treatment chamber part 4 via a tapering of its outer diameter r. The annular gap formed between the treatment chamber part 4 and the nozzle 21 is sealed in a liquid-tight manner against the penetration of process medium via a sealing element 24. Between the gasket 20 and the end face of the treatment chamber part 4 facing the process container, another ring seal 25, supplementally serving as a wiping ring, is pressed in.

The support structure 5 includes a first radial passageway 26, which aligns with the radial passageway 14 of the treatment chamber part 4, so that through the aligning of passageways 26 and 14, treatment medium can be fed into the treatment chamber 13. Correspondingly, the support structure 5 includes an additional radial passageway 27 aligning with the passageway 15 of the treatment chamber part 4, in order to conduct treatment medium out of the treatment chamber 13. In order to assure the aligned orientation of the passageways 14, 15 of the treatment chamber part 4 with the support structure 5, a twisting of the treatment chamber part 4 with respect to the support structure 5 is inhibited via a twist-preventer. The twist-preventer includes, in the example shown here, a set pin 28, which is held elastically in the connector apparatus-end inner wall of the support structure 5 and engages into a cavity of the treatment chamber part 4.

Figure 4:
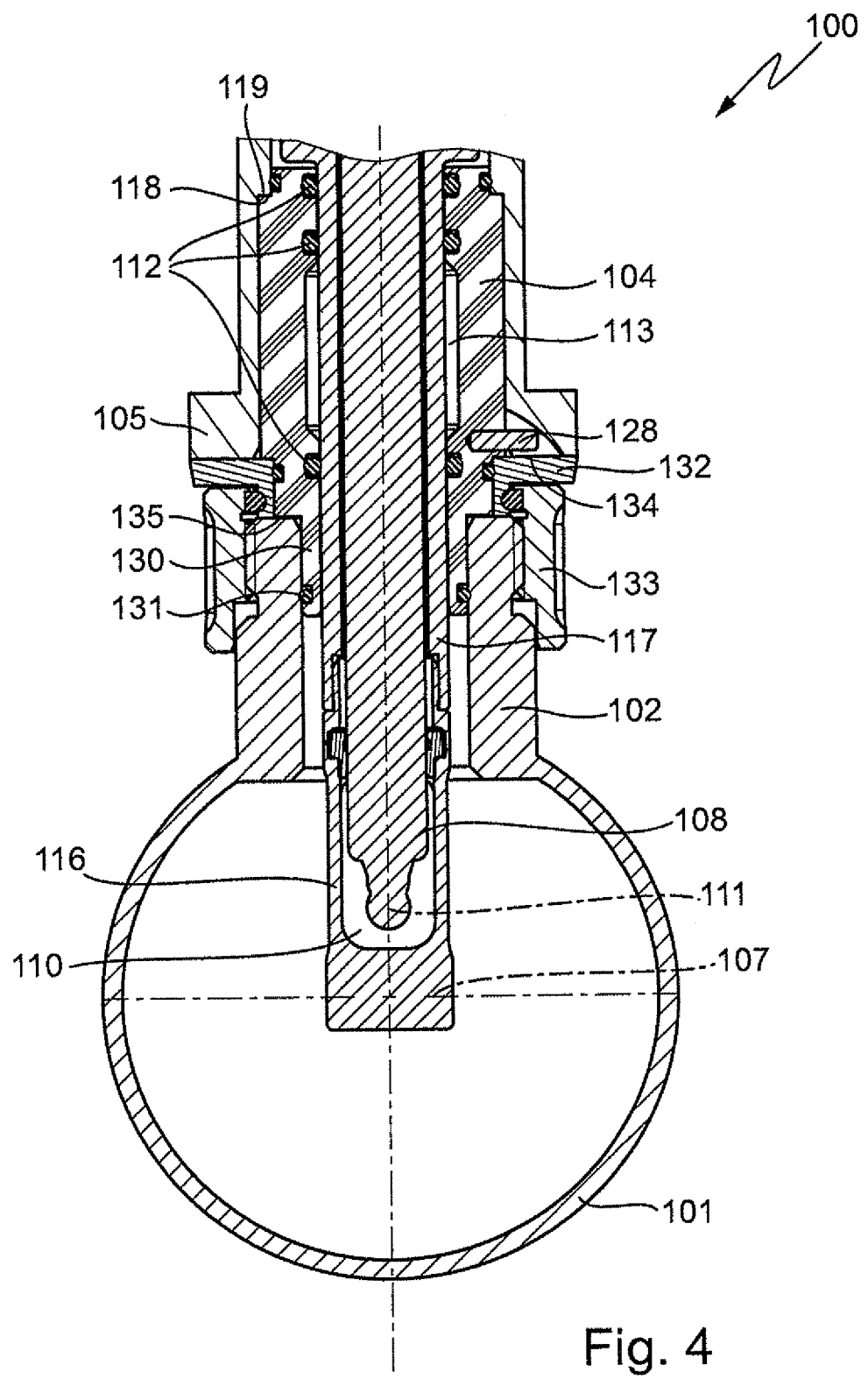
FIG. 4 a probe system according to a second embodiment for connection to a nozzle of a process container, in measuring position.
Figure 5:
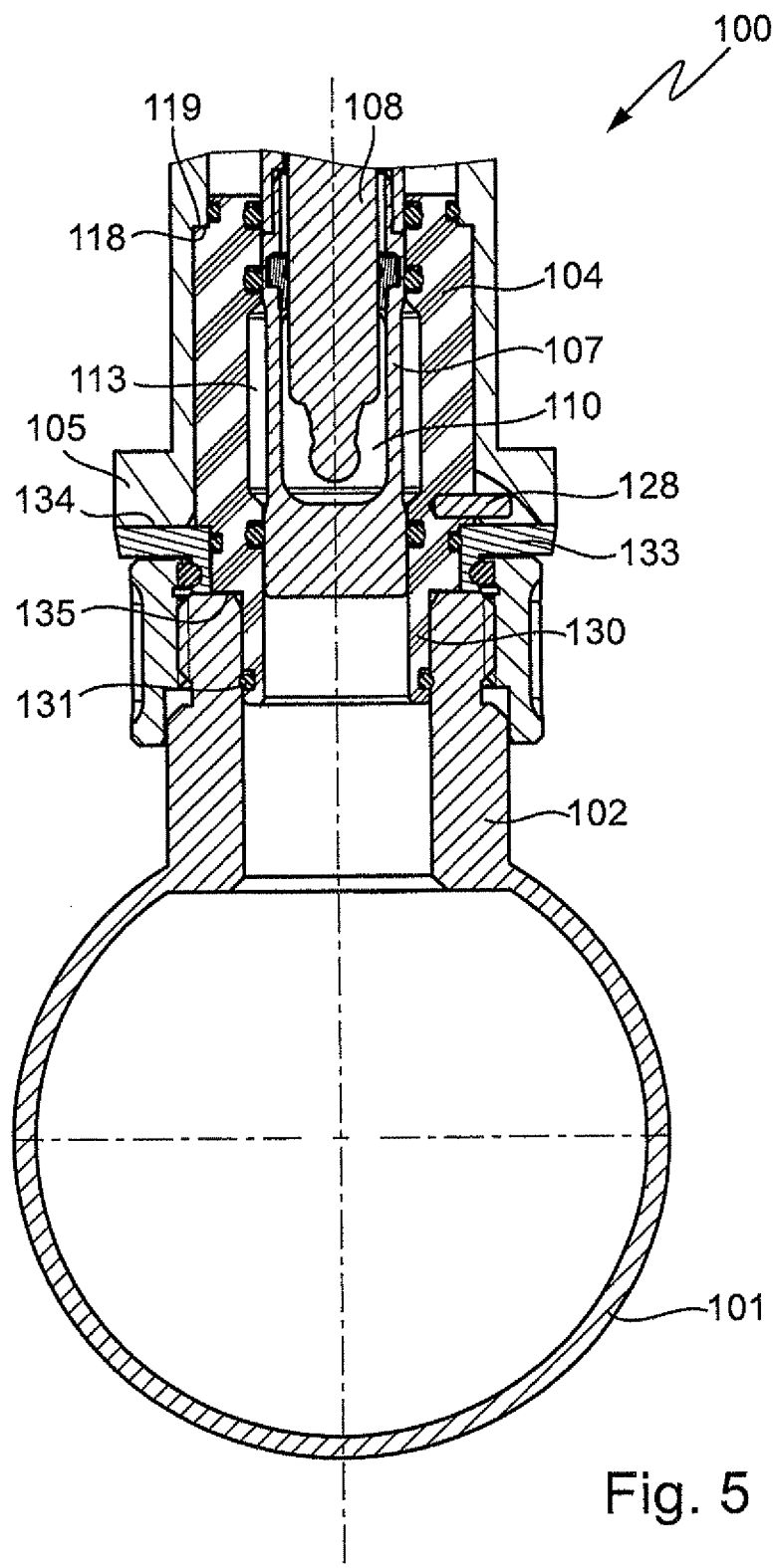
FIG. 5 the probe system shown in FIG. 4, in treatment position.

FIGS. 4 and 5 show a second example of a probe system 100, which is embodied to be connected to a process container 101 having a connection nozzle 102. FIG. 4 shows the probe system 101 with the immersion tube 107 in the measuring position, while FIG. 5 shows the probe system 101 with the immersion tube 107 in the treatment position.

Probe system 100 includes, like the probe system 1 described based on FIGS. 2 and 3, a drive system (not shown in FIGS. 4 and 5) for axial movement of the immersion tube 107. The drive system for FIGS. 4 and 5 is, for example, pneumatically or manually actuatable. Immersion tube 107 is, in a manner equivalent to the immersion tube 7 of the apparatus shown in FIGS. 2 and 3, embodied with a frontal protective cylinder, and a section following behind the protective cylinder with perforations 110, through which the measuring head 111 of the measuring probe 108 accommodated in the immersion tube is contactable with process medium, or, in the treatment position, with a treatment medium. Immersion tube 107 is formed of a front, medium-contacting, first immersion tube part 116, and a second immersion tube part 117 connected therewith via a screw thread connection or bayonet connection. The second immersion tube part 117 is connected with the movable part of the drive system directly, or via one or more intermediate pieces. The medium-contacting, first immersion tube part 116 is composed of a material chemically inert with respect to the process medium and with respect to the treatment medium, for example, a synthetic material such as PFA, PTFE or PEEK, while the second immersion tube part 117 need not be formed of an inert material.

Immersion tube 107 is guided in a treatment chamber part 104 embodied as an essentially tubular sleeve surrounding the treatment chamber 113. Treatment chamber part 104 has a series of grooves lying on the inside, in which ring seals 112 are held. The ring seals 112 bear against the immersion tube 107. Via a widening of the inner diameter of the treatment chamber part 104 between the two ring seals 112, between the immersion tube 107 and the treatment chamber part 104, an annular gap is formed, which serves as treatment chamber 113. By means of the ring seals 112 bounding the treatment chamber 113, treatment chamber 113 is sealed off in a liquid-tight manner from the process container 101, and, on the rear side, from the drive system (not shown in FIGS. 4 and 5).

The treatment chamber part 104 is surrounded by a support structure 105, which, in the example shown here, is formed as a one-piece, essentially tubular, sleeve that surrounds treatment chamber part 104. The treatment chamber part 104 includes a number of passageways (not shown in FIGS. 4 and 5) extending in a radial direction and communicating with the treatment chamber 113, in order to supply a treatment liquid to the treatment chamber, or to remove this from the treatment chamber. The support structure 105 includes an equal number of radial passageways aligning with the radial passageways of the treatment chamber part 104, so that treatment media can be supplied to the treatment chamber 113 externally through the support structure 105, and can be removed therefrom again. The passageways of the treatment chamber part 104 and the support structure 105 can be embodied, for example, in an equal manner as in the example of an embodiment shown in FIGS. 2 and 3. As in the example of an embodiment described in FIGS. 2 and 3, a twisting motion between the treatment chamber part 104 and the support structure 105 of the probe system 100 shown in FIGS. 4 and 5 can be inhibited by means of a twist-preventer. The twist-preventer can comprise, for example, a locking pin 128 held elastically in the support structure 105 and engaging in a radial cavity in the opposite-lying side wall of the treatment chamber part 104.

On the connector apparatus-end, the treatment chamber part 104 includes a plug-like, tubular projection 130, which is embodied so as to enter into the connection nozzle 102 of the process container 101. In an outer wall of the projection 130, an annular groove is formed, in which an outwardly lying ring seal 131 is accommodated, which bears against the inner wall of the connection nozzle 102.

For forming a stable mechanical connection between the probe system 100 and the connection nozzle 102 of the process container 101, the probe system 100 includes a holding ring 132, which, by means of a coupling nut 133, is fixable on the connection nozzle 102. The holding ring 132 includes a bearing and securement surface 134 for the support structure 105, which faces away from the connector apparatus, and on which the support structure 105 is, for example, secured via a screwed connection. The holding ring 132, together with the end region of the connection nozzle 102 connecting to the holding ring 132 in the process-side direction, forms a counterbearing, on which the treatment chamber part 104 is supported via an annular step 135 formed by a step-like tapering of its outer diameter. The holding ring 132 and the support structure 105 can be formed as non-medium-contacting parts from a stable, not necessarily chemically inert material, such as, for example, a high quality alloy steel, even stainless steel, so that a stable holding of the probe system 100 and a sufficient stability of the probe system 100 per se is assured.

In the end region of the treatment chamber part 104 facing away from the connector apparatus, the outer diameter of the treatment chamber part 104 tapers stepwise, and thus forms an annular shoulder 118, on which an abutment surface formed in the inner wall of the support structure 105 and facing the connector apparatus 119 abuts.

The medium-contacting treatment chamber part 104 can be formed from a chemically inert, under certain circumstances less mechanically stable material, for example, a synthetic material such as PEEK, PTFE, PFA or PVDF. Since treatment chamber part 104 is held by means of the holding ring 132 and shape-interlockingly at its end opposite the holding ring 132 by the support structure 105, an exceptional mechanical stability of the treatment chamber part 104 is not required.

Especially advantageously in the case of the examples of embodiments shown in FIGS. 2 to 5 is, moreover, that the sealing elements, which seal the process container from the environment and from the treatment chamber, are held in grooves of the treatment chamber part. All sealing elements are thus easily accessible for replacement via the treatment chamber part of the probe system being removed, which significantly simplifies maintenance of the probe system.

The invention claimed is:

1. A probe system for measuring a measured variable of a process medium contained in a process container, comprising:
   a connector apparatus connectable with connecting means of the process container;
   a treatment chamber part forming a treatment chamber and having at least one treatment medium supply line communicating with said treatment chamber,
   a measuring probe with a measuring head embodied for registering measured values, wherein said measuring probe is accommodated in an immersion tube seated so as to be axially shiftable between a measuring position, in which said measuring head is arranged outside said treatment chamber, and a treatment position, in which said measuring head is retracted into said treatment chamber, said immersion tube, on its connector apparatus-side front end, has a front-end closed, protective cylinder, and said measuring head is arranged in a perforated section of said immersion tube behind said protective cylinder, so that, in the measuring position of said immersion tube, said measuring head is contactable via perforations with the process medium, and in the treatment position of said immersion tube, is contactable with the treatment medium; and
   a drive system for axial shifting of the immersion tube, arranged on the end region of the probe system facing away from said connector apparatus, wherein:
   said treatment chamber part is surrounded by a support structure connected with said connector apparatus and with said drive system;
   wherein said support structure is embodied as a sleeve at least sectionally having a tubular wall and accommodating said treatment chamber part;
   said sleeve has at least one passageway extending through said tubular wall; and
   said treatment chamber part and said support structure are arranged, secured against testing, in an orientation relative to one another, in which said at least one passageway aligns with a supply line serving to convey treatment medium and communicating with said treatment chamber.

2. The probe system as claimed in claim 1, wherein:
   said treatment chamber part is formed of a material, that is chemically inert.

3. The probe system as claimed in claim 2, wherein:
   the synthetic material comprises PVDF (polyvinylidene fluoride), PEEK, PFA (perfluoroalkoxy alkane), PTFE (polytetrafluoroethylene).

4. The probe system as claimed in claim 1, wherein:
   all components of the probe system, which in a position of said immersion tube, come in contact with the process medium, are formed of a chemically inert material.

5. The probe system as claimed in claim 1, wherein:
said treatment chamber part, by means of said support structure, is secured to said connector apparatus in a shape-interlocking manner.

6. The probe system as claimed in claim 1, wherein:
said connector apparatus includes a flange connected with said support structure, which is connectable, with interpositioning of an annular gasket, to a complementary flange of said process container.

7. The probe system as claimed in claim 6, wherein:
a connector apparatus-end of said treatment chamber part has an annular shoulder, which sits in a seat formed by an axially extending port of said annular gasket; and
a gap formed between said seat and said treatment chamber part is sealed from the process container by means of at least one ring seal.

8. The probe system as claimed in claim 7, wherein:
said seat formed in said port of said axially extending gasket has an annular groove, in which is accommodated a wiping ring bearing against said immersion tube.

9. The probe system as claimed in claim 6, wherein:
said gasket is composed of the same material as said treatment chamber part.

10. The probe system as claimed in claim 1, wherein:
said treatment chamber part has on its connector apparatus-end a plug-like projection, which is embodied so as to enter into a complementary port of said process container; and
said connector apparatus includes a holding ring, which is securable to said complementary port by means of a coupling nut, and which has an annular area facing away from the process container, on which bears an annular step formed in the outer wall of said treatment chamber part.

11. A probe system for measuring a measured variable of a process medium contained in a process container, comprising:
a connector apparatus connectable with connecting means of the process container;
a treatment chamber part forming a treatment chamber and having at least one treatment medium supply line communicating with said treatment chamber,
a measuring probe with measuring head embodied for registering measured values, wherein said measuring probe is accommodated in an immersion tube seated so as to be axially shiftable between a measuring position, in which said measuring head is arranged outside said treatment chamber, and a treatment position, in which said measuring head is retracted into said treatment chamber, said immersion tube, on its connector apparatus-side front end, has a front-end closed, protective cylinder, and said measuring head is arranged in a perforated section of said immersion tube behind said protective cylinder, so that, in the measuring position of said immersion tube, said measuring head is contactable via perforations with the process medium, and in the treatment position of said immersion tube, is contactable with the treatment medium; and
a drive system for axial shifting of the immersion tube, arranged on the end region of the probe system facing away from said connector apparatus;
wherein said treatment chamber part is surrounded by a support structure connected with said connector apparatus and with said drive system; and
said treatment chamber part, by means of said support structure, is secured to said connector apparatus in a shape-interlocking manner.

12. The probe system as claimed in claim 11, wherein:
said treatment chamber part is formed of a material that is chemically inert.

13. The probe system as claimed in claim 12, wherein:
the synthetic material comprises PVDF (polyvinylidene fluride), PEEK, PFA (perfluroalkoxy alkane), PTFE (polytetrafluoroethylene).

14. The probe system as claimed in claim 11, wherein:
all components of the probe system, which in a position of said immersion tube come in contact with the process medium, are formed of a chemically inert material.

15. The probe system as claimed in claim 11, wherein;
said connector apparatus includes a flange connected with said support structure, which is connectable, with interpositioning of an annular gasket, to a complementary flange of said process container.

16. The probe system as claimed in claim 15, wherein:
said gasket is composed of the same material as said treatment chamber part.

17. A probe system for a measuring a measured variable of a process medium contained in a process container, comprising:
a connector apparatus connectable with connecting means of the process container;
a treatment chamber part forming a treatment chamber and having at least one treatment medium supply line communicating with said treatment chamber,
a measuring probe with a measuring head embodied for registering measured values, wherein said measuring probe is accommodated in an immersion tube seated so as to be axially shiftable between a measuring position, in which said measuring head is arranged outside said treatment chamber,and a treatment position, in which said measuring head is retracted into said treatment chamber said immersion tube, on its connector apparatus-side front end, has a front-end closed, protective cylinder, and said measuring head is arranged in a perforated section of said immersion tube behind said protective cylinder, so that, in the measuring position of said immersion tube, said measuring head is contactable via perforations with the process medium, and in the treatment position of said immersion tube, is contactable with the treatment medium; and
a drive system for axial shifting of the immersion tube, arranged on the end region of the probe system facing away from said connector apparatus;
wherein said treatment chamber part is surrounded by a support structure connected with said connector apparatus and with said drive system;
said connectable, with interpositioning of an annular gasket, to a complementary flange of said process container;
a connector apparatus-end of said treatment chamber part has an annular shoulder, which sits in a seat formed by an axially extending port of said annular gasket; and
a gap formed between said seat and said treatment chamber part is sealed from the process container by means of at least one ring seal.

18. The probe system as claimed in claim 17, wherein:
said treatment chamber part is formed of a material that is chemically inert.

19. The probe system as claimed in claim 18, wherein:
the synthetic material comprises PVDF (polyvinylidene fluride), PEEK, PFA (perfluroalkoxy alkane), PTFE (polytetrafluroethylene).

20. The probe system as claimed in claim 17, wherein:
all components of the probe system, which in a position of said immersion tube come in contact with the process medium, are formed of a chemically inert material.

* * * * *